US010918303B2

(12) United States Patent
Rappel et al.

(10) Patent No.: US 10,918,303 B2
(45) Date of Patent: Feb. 16, 2021

(54) SYSTEM AND METHOD TO DETERMINE DRIVING SOURCES OF HEART RHYTHM DISORDERS

(71) Applicant: THE REGENTS OF THE UNIVERSITY OF CALIFORNIA, Oakland, CA (US)

(72) Inventors: Wouter-Jan Rappel, San Diego, CA (US); David Vidmar, San Diego, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 72 days.

(21) Appl. No.: 16/087,552

(22) PCT Filed: Mar. 24, 2017

(86) PCT No.: PCT/US2017/024115
§ 371 (c)(1),
(2) Date: Sep. 21, 2018

(87) PCT Pub. No.: WO2017/165830
PCT Pub. Date: Sep. 28, 2017

(65) Prior Publication Data
US 2019/0223743 A1 Jul. 25, 2019

Related U.S. Application Data

(60) Provisional application No. 62/312,849, filed on Mar. 24, 2016.

(51) Int. Cl.
A61B 5/04 (2006.01)
A61B 5/0468 (2006.01)
(Continued)

(52) U.S. Cl.
CPC ............ *A61B 5/0468* (2013.01); *A61B 5/044* (2013.01); *A61B 5/0422* (2013.01);
(Continued)

(58) Field of Classification Search
CPC ... A61B 5/0468; A61B 5/0464; A61B 5/6869; A61B 5/6852; A61B 5/0422;
(Continued)

(56) References Cited

U.S. PATENT DOCUMENTS 8,521,266 B2    8/2013  Narayan et al.
8,700,140 B2    4/2014  Narayan et al.
(Continued)

OTHER PUBLICATIONS

Kalifa, J, et al. "Mechanisms of wave fractionation at boundaries of high-frequency excitation in the posterior left atrium of the isolated sheep heart during atrial fibrillation," Circulation, vol. 113, No. 5, Feb. 7, 2006, pp. 626-633.
(Continued)

Primary Examiner — Mallika D Fairchild
(74) Attorney, Agent, or Firm — Eleanor Musick; Musick Davison LLP

(57) ABSTRACT

A method and system for determining a source of a cardiac rhythm disorder includes collecting cardiac signals at a plurality of locations during a cardiac arrhythmia and identifying activation times within the cardiac signals. After computing the time-dependent phase of each region of tissue, a level of phase synchrony is determined between each pair of locations to assign a synchronization number for each pair of locations. Using the synchronization number, a spatial synchrony map is generated to identify one or more asynchronous tissue regions surrounded by regions of synchrony in the patient's heart.

21 Claims, 5 Drawing Sheets

(51) Int. Cl.
*A61B 5/0464* (2006.01)
*A61N 1/368* (2006.01)
*A61B 5/00* (2006.01)
*A61B 5/042* (2006.01)
*A61B 5/044* (2006.01)
*A61B 5/0245* (2006.01)

(52) U.S. Cl.
CPC .......... *A61B 5/0464* (2013.01); *A61B 5/6823* (2013.01); *A61B 5/6852* (2013.01); *A61B 5/6869* (2013.01); *A61B 5/7235* (2013.01); *A61N 1/368* (2013.01); *A61B 5/0002* (2013.01); *A61B 5/0245* (2013.01); *A61B 5/686* (2013.01); *A61B 5/7246* (2013.01)

(58) Field of Classification Search
CPC ..... A61B 5/6823; A61B 5/044; A61B 5/7235; A61B 5/7246; A61B 5/686; A61B 5/0002; A61B 5/0245; A61N 1/368
See application file for complete search history.

(56) References Cited

U.S. PATENT DOCUMENTS

| | | |
|---|---|---|
| 8,838,222 B2 | 9/2014 | Narayan et al. |
| 8,838,223 B2 | 9/2014 | Narayan et al. |
| 8,868,169 B2 | 10/2014 | Narayan et al. |
| 9,089,269 B2 | 7/2015 | Narayan et al. |
| 9,241,667 B2 | 1/2016 | Narayan et al. |
| 9,375,156 B2 | 6/2016 | Narayan et al. |
| 9,380,950 B2 | 7/2016 | Narayan et al. |
| 9,439,573 B2 | 9/2016 | Narayan et al. |
| 9,549,684 B2 | 1/2017 | Narayan et al. |
| 9,717,436 B2 | 8/2017 | Narayan et al. |
| 9,955,879 B2 | 5/2018 | Narayan et al. |
| 10,092,196 B2 | 10/2018 | Narayan et al. |
| 2001/0039443 A1 | 11/2001 | Chen |
| 2002/0010392 A1 | 1/2002 | Desai |
| 2003/0236466 A1 | 12/2003 | Tarjan et al. |
| 2004/0059237 A1 | 3/2004 | Narayan et al. |
| 2010/0156898 A1 | 6/2010 | Voros et al. |
| 2010/0198283 A1 | 8/2010 | Zhang et al. |
| 2012/0283590 A1 | 11/2012 | Afonso |

OTHER PUBLICATIONS

Masse, S., et al., "Wave similarity of human ventricular fibrillation from bipolar electrograms", Eurospace (2007) vol. 9, pp. 10-19.

Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.

Narayan, S.M. et al.; "Clinical Mapping Approach to Disagnose Electrical Rotors and Focal Impulse Sources for Human Atrial Fibrillation"; J. Cardiovasc Electrophysiol., May 2012, vol. 23(5), pp. 447-454.

Narayan, S.M. et al.; "Repolarization and Activation Restitution Near Human Pulmonary Veins and Atrial Fibrillation Initiation: Mechanisms Separating Persistent From Paroxysmal AF"; J. Am Coll Cardiol., Oct. 7, 2008, vol. 52(15), pp. 1222-1230.

PCT/US2017/024142, International Search Report and Written Opinion, dated Jun. 19, 2017, 8 pages.

Sahadevan, J., K. Ryu, et al. "Epicardial Mapping of Chronic Atrial Fibrillation in Patients: Preliminary Observations." Circulation; 2004; vol. 110(21): p. 3293-3299.

Sanders, P., et al., "Spectral Analysis Identifies Sites of High-Frequency Activity Maintaining Atrial Fibrillation in Humans." Circulation, 2005, vol. 112(6): pp. 789-797.

Skanes, A. C. et al.; "Spatiotemporal Periodicity During Atrial Fibrillation in the Isolated Sheep Heart." Circulation, 1998, vol. 98(12): pp. 1236-1248.

Tabereaux P. B., et al.; "Activation patterns of Purkinje fibers during long-duration ventricular fibrillation in an isolated canine heart model." Circulation, 2007, vol. 116(10): pp. 1113-1119.

Vidmar D. et al., "Phase synchrony reveals organization in human atrial fibrillation", Am J Heart Circ Physiol, 2015, vol. 309; pp. H2118-2126.

PCT/US2017/024115 International Search Report and Written Opinion dated Jun. 6, 2017, 9 pages.

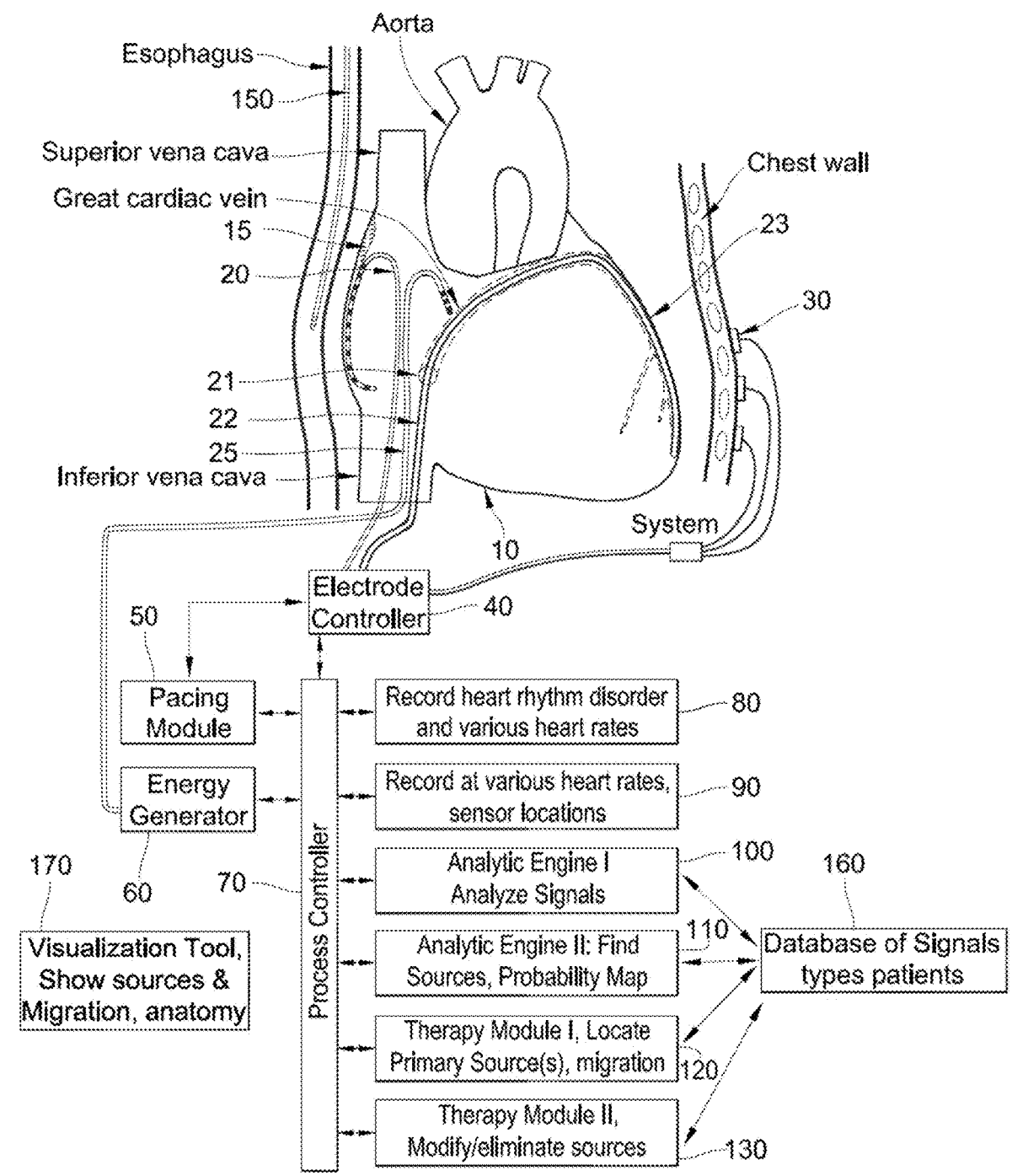
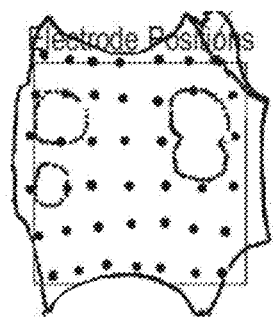
FIG. 1A
FIG. 1B

SYSTEM AND METHOD TO DETERMINE DRIVING SOURCES OF HEART RHYTHM DISORDERS

RELATED APPLICATIONS

This application is a 371 national stage filing of International Application No. PCT/US2017/024115, filed Mar. 24, 2017, which claims the benefit of the priority of U.S. Provisional Application No. 62/312,849, filed Mar. 24, 2016, each of which is incorporated herein by reference in its entirety.

GOVERNMENT RIGHTS

This invention was made with government support under Grant No. HL122384 awarded by the National Institutes of Health. The government has certain rights in the invention.

FIELD OF THE INVENTION

The present invention relates to a method and system and machine for diagnosing and locating the source for, and treating, heart rhythm disorders, and more particularly to a method for identifying tissue regions in the heart that exhibit distinct patterns of synchrony.

BACKGROUND

Heart rhythm disorders, including ventricular fibrillation (VF) and atrial fibrillation (AF), are common, life-threatening arrhythmias. Atrial fibrillation (AF) is a serious health condition that affects over 30 million people worldwide, resulting in an increased risk of stroke, heart failure, and mortality. During AF, the organization of electrical activity in the atria no longer consists of a wave that propagates from the sino-atrial node to the atrioventricular node in an organized fashion. Instead, tissue excitation is irregular resulting in a reduced ability to pump and a reduced blood flow.

VF is a major cause of the 400,000 cases of Sudden Cardiac Death (SDC) in the United States while AF, the most common heart rhythm disorder (cardiac arrhythmia) in the United States, may cause substantial morbidity and mortality. Due to its inherent complexity, our understanding of the sustaining mechanisms of these heart rhythm disorders remains incomplete.

While understanding the specific mechanisms that drive and sustain AF is of key importance in selecting effective treatments for the disease, many of its underlying dynamical features and initiation mechanisms remain poorly understood. Triggers from the pulmonary veins, in the form of ectopic beats, have been demonstrated to participate in the initiation of AF, and traditional ablation techniques attempt to isolate these veins. Unfortunately, these procedures have limited long-term success.

Several mapping modalities and techniques exist that are capable of registering activation dynamics at multiple locations within the ventricles or atria. For example, high-resolution basket electrodes can register electrograms at multiple locations of the heart. These electrograms, or the activation times determined from the electrograms, can be used to compute phase maps. Visual inspection of these maps is currently employed to identify the location of stable sources that drive the rhythm disorders. Targeted ablation of these sources has been shown to be an effective treatment for VF and AF.

Recordings from 64-pole basket electrodes demonstrate that spiral waves may be spatially conserved in patients, with tip locations that can remain in reproducible atrial regions for months at a time until eliminated. External noninvasive mapping has also demonstrated that the location of reentries recurred repetitively in the same region. The importance of spiral waves in the maintenance of AF is supported by reports from several groups showing that limited ablation at localized spiral waves or focal sources may improve long-term outcome compared with traditional ablation techniques.

Identification of the appropriate target for ablation can be a challenge because current tools to identify and locate the cause of the heart rhythm disorder are less than optimal, limiting efforts to precisely deliver energy to the region needed to terminate and eliminate the disorder without collateral damage to otherwise healthy regions of the heart. For human AF, particularly persistent AF, the absence of identified and located causes means that ablation is empiric and often involves damage to approximately 30-40% of the atrium that could theoretically be avoided if the cause(s) were identified and located for minimally invasive ablation and/or surgical therapy (Cox 2005). In persistent AF, a highly prevalent form of AF, ablation has a single procedure success rate of only 50-60% (Cheema, Vasamreddy et al. 2006; Calkins, Brugada et al. 2007) despite lengthy 4-5 hour procedures and a 5-10% rate of serious complications (Ellis, Culler et al. 2009) including death (Cappato, Calkins et al. 2009).

Existing systems display data that the practitioner must still interpret based on experience—there is no widely-available tool to directly identify and locate the cause of the disorder to enable the practitioner to detect, diagnose and treat it. Such systems are based on currently used methods described in, for example, U.S. Pat. Nos. 5,662,108, 5,662, 108, 6,978,168, 7,289,843 and others by Beatty and coworkers, U.S. Pat. No. 7,263,397 by Hauck and Schultz, U.S. Pat. No. 7,043,292 by Tarjan and coworkers, U.S. Pat. No. 6,892,091 and other patents by Ben-Haim and coworkers and U.S. Pat. No. 6,920,350 by Xue and coworkers. These methods and instruments detect, analyze and display electrical potentials, often in sophisticated 3-dimensional anatomic representations, but still fail to identify and locate the cause of heart rhythm disorders, particularly for complex disorders such as AF and VF. This is also true for patents by Rudy and coworkers (U.S. Pat. Nos. 6,975,900 and 7,016, 719, among others), which use signals from the body surface to "project" potentials on the heart.

Certain known methods for identifying and locating causes for heart rhythm disorders may work in simple rhythm disorders, but are not useful for identifying causes of complex disorders such as AF, VF or polymorphic VT. Activation mapping (tracing activation back to the earliest site) is useful only for simple tachycardias, works poorly for Atrial Flutter (AFL, a continuous rhythm without a clear "start"), and not at all for AF with variable activation paths. Entrainment mapping uses pacing to identify sites where the stimulating electrode is at the cause of a rhythm, yet pacing cannot be applied in AF and even some "simple" rhythms such as atrial tachycardias due to automatic mechanisms. Stereotypical locations are known for the cause(s) of atrioventricular node reentry, typical AFL and patients with early (paroxysmal) AF, but not for the vast majority of patients with persistent AF (Calkins, Brugada et al. 2007), VF and other complex disorders.

Prior methods have largely focused on mapping of the anatomy to identify whether a patient has a heart disorder, rather than determining the cause or source of the disorder. Thus, there is an urgent need for methods and tools to directly identify and locate causes for heart rhythm disorders in individual patients to enable curative therapy. This is particularly critical for AF and other complex rhythm disorders for which, ideally, a system would detect localized causes for ablation by minimally invasive, surgical or other methods.

The mechanisms for the maintenance of AF in general, and spiral wave dynamics, in particular, are still under debate. There are two competing paradigms: multiwavelet reentry (MWR) and stable spiral wave induced breakup (SSWIB). The multiwavelet hypothesis posits that the complex activation patterns observed during AF are caused by a multitude of short-lived spiral waves with limited spatial extent (wavelets). Crucial in this scenario is that these wavelets are unstable and continuously fragment and generate offspring wavelets, resulting in a stochastic pattern of activation. MWR was first described in the modeling work of Moe et al., "A Computer Model of Atrial Fibrillation," *Am Heart J*, 20, 67 (1964), and was studied in further detail in both computer models and in animal models. Notably, MWR depends solely on the instability of the spiral wave and can thus occur in homogeneous as well as heterogeneous tissue.

During SSWIB, activation from one or more spatially conserved spiral waves breaks down away from the tip, a process known as fibrillatory conduction. In this scenario, the stable spiral waves, or mother rotors, are the driving sources of fibrillation and complex activation patterns arise from breakup distant to the stable spiral cores. In contrast to MWR, this scenario requires tissue heterogeneity, either in the form of conduction anisotropy, cellular heterogeneity, or tissue geometry. This is because in completely homogeneous tissue the driving spirals would either destabilize, resulting in MWR, or would control the entire domain, leading to regular activation consistent with atrial flutter or organized tachycardia (AT). This scenario also implies that not all regions contribute equally to the maintenance of fibrillation and that the regions harboring spirals are the most important. This is in sharp contrast to MWR where there are no privileged regions and the fragmentation is self-sustaining and the result of inherent tissue instability.

As described by Narayan and Rappel in U.S. Pat. Nos. 8,521,266, 8,838,222 and 8,838,223, each of which is incorporated herein by reference, computational methods for analyzing physiological signals generate activation patterns that can be used to identify sources of heart rhythm disorders in a procedure referred to as "focal impulse and rotor mapping", or "FIRM." The approach for creating "activation trails" used in the FIRM procedure includes phase mapping of signals obtained from multi-electrode sensors, including basket electrodes. Generation of phase maps involves assigning a phase $\varphi$ to the signal at every electrode and at every time point. The phase at the exact location of the tip of the rotor is undefined and summing up the gradient of the phase of neighboring sites results in a "phase jump" of $2\pi$. Thus, a rotor location corresponds to a phase singularity. Mathematically, these phase singularities can be found by evaluating a line integral over a closed curve as $\oint \vec{\nabla}\varphi \cdot d\vec{l} = 2\pi$ where the line integral is taken over a path l surrounding the phase singularity. Since the signal from the electrode is a single observable, the determination of the phase requires special attention. A number of different methods can be employed depending on the quality of the electrode signal.

Determining the location of ablation based on phase maps can be problematic for several reasons: first, the computed phase maps may erroneously assign a mechanism to an area of conduction slowing and wavefront curvature. Second, the visual identification of phase movies is prone to operator error and subjective interpretation. Third, the construction and interpretation of these maps can be time-consuming. Fourth, there is a need for a highly automated way of determining rotational or focal sources.

It is challenging to distinguish between the two hypothesized fibrillatory mechanisms. Although the spatial resolution of techniques such as FIRM have been shown to be able to map human spiral waves, spatial mapping of multiple meandering spiral waves is laborious. First, it requires specialized software to construct these maps. Second, and perhaps more importantly, it necessitates careful interpretation of these maps to identify wave tips and track their trajectory until they annihilate. Thus, a simpler methodology for the interpretation of high-resolution mapping would be advantageous.

BRIEF SUMMARY

According to exemplary embodiments, a system and method identify and locate driving sources of heart rhythm disorders using data obtained from multiple locations to determine spatial synchrony maps. The maps may be used to determine tissue regions that are activated in an asynchronous fashion compared to surrounding tissue. The ability to determine the location of the asynchronous regions may improve anti-arrhythmic therapies. These automated methods do not require subjective, manual interpretation to determine rhythm disorder sources. The inventive approach is based on the identification of tissue regions that activate independently from neighboring tissue, and thus autonomously identify drivers of arrhythmias.

An analysis technique is provided to quantify the synchrony between regions of tissue during human atrial fibrillation (AF). The analysis reveals localized pockets of synchrony during AF, arguing against multiwavelet reentry and suggesting that instead AF involves spatially contiguous regions of coherence surrounded by disorganized activation.

Embodiments of the invention utilize a methodology that focuses on the spatial distribution of temporal information obtained by electrode recordings. Specifically, the degree of phase synchronization between electrodes is examined, a method widely used in biology, including information processing in the brain, in circadian rhythms, and the cardiorespiratory system. Analyzing this synchronization in clinical data provides a simple and quantitative view into underlying conduction dynamics during AF and relies only on the marking of activation times from recorded electrograms. This method can be used to determine regions of synchronization in both in silico and clinical data.

In embodiments disclosed herein, activation times marked directly from electrograms recorded during cardiac arrhythmias are used to compute the time-dependent phase of each region of tissue.

In one aspect of the invention, a method for determining a source of a cardiac rhythm disorder in a patient suspected of having the cardiac rhythm disorder includes: collecting, via a computer processor, a plurality of cardiac signals at a plurality of locations during a cardiac arrhythmia; identifying activation times within the cardiac signals; computing time-dependent phase of each region of tissue; computing a level of phase synchrony between each pair of locations of the plurality of locations to assign a synchronization number for each pair of locations; and generating a spatial synchrony map using the synchronization numbers to identify one or more asynchronous tissue regions surrounded by regions of synchrony in the patient's heart. In one embodiment, the synchronization number between two locations i and j is computed according to relationship $\gamma_{ij}^2 = \langle \cos \psi_{ij} \rangle^2 + \langle \sin \psi_{ij} \rangle^2$, where $\psi_{ij}$ is the cyclic relative phase, $\psi_{ij} = (\varphi_i - \varphi_j) \bmod 2\pi$.

The step of generating may include computing and comparing local and global distributions of synchronization number. Comparison of local and global distributions of synchronization number may further comprise quantifying a difference in the distributions.

In exemplary implementations, a method for quantifying differences in the distributions may be selected from the group consisting of Hellinger distance, the Kullback—Leibler divergence, the Bhattacharyya distance, the Kolmogorov-Smirnov test, and the Chi-Square test.

In an exemplary embodiment, an Asynchronous Index (ASI) is assigned to the difference and is associated with a specific location of the plurality of locations. A map of the ASI may be displayed with visually-encoded regions corresponding to the locations. The visually-encoded regions may be indicated by a visually-distinguishable scale selected from color, grayscale, and alphanumeric character labels. The method may also include, prior to collecting, inducing the cardiac arrhythmia.

In another aspect of the invention, a system for determining a source of a cardiac rhythm disorder in a patient suspected of having the cardiac rhythm disorder includes: a computer processor programmed to execute the steps of: collecting a plurality of cardiac signals at a plurality of locations during a cardiac arrhythmia; identifying activation times within the cardiac signals; computing time-dependent phase of each region of tissue; computing a level of phase synchrony between each pair of locations of the plurality of locations to assign a synchronization number for each pair of locations; and generating a spatial synchrony map using the synchronization numbers to identify one or more asynchronous tissue regions surrounded by regions of synchrony in the patient's heart. In one embodiment, the synchronization number for locations i and j is computed according to relationship $\gamma_{ij}^2 = \langle \cos \psi_{ij} \rangle^2 + \langle \sin \psi_{ij} \rangle^2$, where $\psi_{ij}$ is the cyclic relative phase, $\psi_{ij} = (\varphi_i - \varphi_j) \bmod 2\pi$. The computer processor may be further programmed to compute and compare local and global distributions of synchronization number. Comparison of local and global distributions of synchronization number may further include quantifying a difference in the distributions. In exemplary implementations, a method for quantifying differences in the distributions may be selected from the group consisting of Hellinger distance, the Kullback—Leibler divergence, the Bhattacharyya distance, the Kolmogorov-Smirnov test, and the Chi-Square test.

In an exemplary embodiment, an Asynchronous Index (ASI) is assigned to the difference and is associating with a specific location of the plurality of locations. The system may further include a visual display device on which a map of the ASI may be displayed with visually-encoded regions corresponding to the locations. The visually-encoded regions may be indicated by a visually-distinguishable scale selected from color, grayscale, and alphanumeric character labels. The system may further include a device for inducing the cardiac arrhythmia and/or a sensor array defining a grid corresponding to locations within the patient's heart.

BRIEF DESCRIPTION OF THE DRAWINGS

FIG. 1A is a schematic diagram of a system for use in embodiments of the invention; FIG. 1B is a two-dimensional representation of a matrix of sensors shown as points or positions superimposed on a cardiac atrial surface.

DETAILED DESCRIPTION OF EMBODIMENTS OF THE INVENTION

Figure 2:
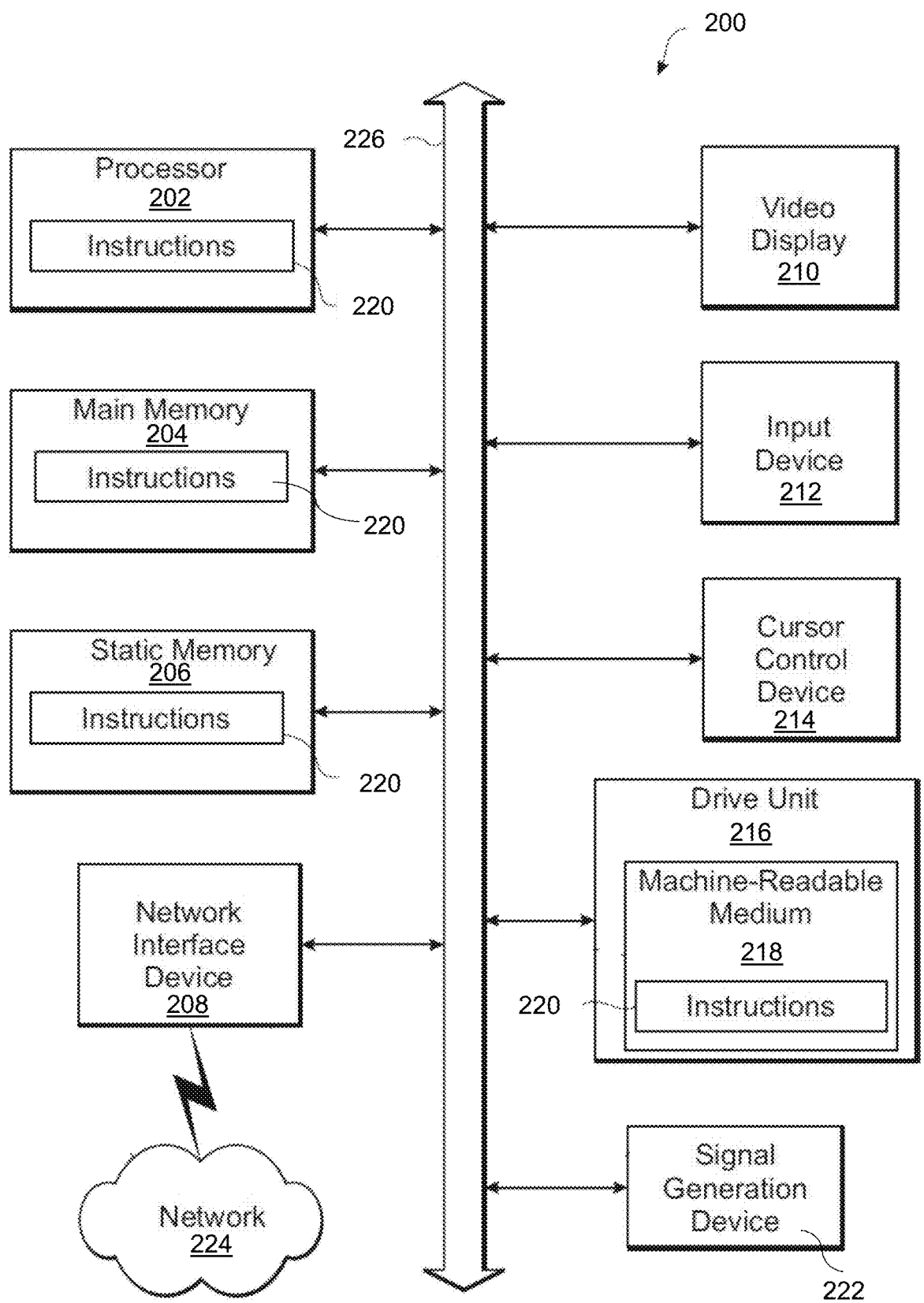
FIG. 2 is a block diagram of a computer system in accordance with the disclosed embodiments.

Definitions:

For purposes of this description, the following definitions will apply:

"Detecting/Diagnosing": The terms detecting and diagnosing a rhythm disorder are used interchangeably in this application.

"Activation time" means the time of activation onset for a given heart signal.

"Activation time duration" means the time period and the signal waveform between the times of activation onset and offset for the signal of a given heartbeat. Diastolic interval is the time period from activation offset of the prior beat to activation onset of the present beat.

"Activation trail" means the ordering of the activation time onset at the sensor locations to create a discernible signature pattern, for example, including without limitation a rotational pattern around a core region indicative of a rotor, a radially emanating pattern from a core region, indicative of a focal beat cause, or a dispersed pattern, requiring further signal sampling and repeating of above analysis steps.

"Identify and locate" means the process of discerning the presence of a localized or dispersed cause of the heart rhythm disorder, then locating said cause relative to sensor locations or relative to known anatomic positions in the heart.

"Heart rhythm disorder" means an abnormal rhythm, often requiring treatment. These include without limitation, rapid rhythms of the top chambers of the heart (atria) such as rapid and abnormal activation of the normal sinus node (inappropriate sinus tachycardia or sinus node reentry), atrial tachycardia (AT), supraventricular tachycardia (SVT), atrial flutter (AFL), premature atrial complexes/beats (PAC) and the complex rhythms of atrial fibrillation (AF) and certain forms of atypical atrial flutter. Rapid rhythms can also occur in the bottom chambers of the heart (ventricles), including such as ventricular tachycardia (VT), ventricular fibrillation (VF), torsades de pointes and premature ventricular complexes/beats (PVC). Heart rhythm disorders can also be slow, including sinus bradycardia, ectopic atrial bradycardia junctional bradycardia, atrioventricular block and idioventricular rhythm.

"Cause of biological or heart rhythm disorder", which is used interchangeably with "source of the biological or heart rhythm disorder" in this application, refers to, without limitation, a rotational pattern of activation sequence around a core region indicative of a rotor, a radially emanating pattern from a core region indicative of a focal beat cause, or a dispersed pattern. In this invention, when a dispersed cause is found, signal sampling is extended to additional multiple locations and the detection and analysis steps of the invention are repeated. These causes are directly responsible for the perpetuation of the heart rhythm disorder.

"Sensor", which is used interchangeably with "electrode", refers to an apparatus for detecting and transmitting signals from the heart or to the heart.

FIG. 1A provides a schematic of various useful components (modules) that may be used in the process and system of the invention. The modules may be separate from each other and cooperatively interfaced to provide their function, or one or more of them may be integrated with each other of contained in the processor, such that the system has less separate hardware units. FIG. 1 depicts an embodiment that allows a cause of the disorder to be localized during a minimally invasive percutaneous procedure, or other procedures such as using surface ECG, a magnetocardiogram, an echocardiographic and/or Doppler measurements from ultrasound, electromagnetic radiation, sound waves, microwaves, or electrical impedance changes.

In FIG. 1A, electrical events in the heart 10 are recorded with sensing electrodes. These electrodes may be catheters 20 placed within the chambers or vasculature of the heart, including basket electrodes and custom-designed recording catheters. The electrodes may also be extensions of leads from an implanted pacemaker or cardioverter-defibrillator, catheters used to record monophasic action potentials or other signals that typically arrive via the vena cavae or coronary sinus 22. FIG. 1B provides an example of a two-dimensional representation of a matrix or array of sensors shown as points or positions superimposed on a cardiac atrial surface, indicated by the irregular shape. The irregular shape represents the left atrium, cut horizontally through the plane of the mitral valve with the two halves folded up and down. Thus, the top portion of the shape corresponds to the superior mitral valve and the lower portion represents the inferior mitral value.

Referring again to FIG. 1A, electrodes 23 may record from the endocardial, epicardial, or pericardial surface of the heart, accessed via electrodes 21 in the coronary sinus, via the electrodes 23 in the pericardial space or other routes. Electrodes may be located in proximity to the nerves supplying the heart 15, which may be located in the left atrium and ventricles. Electrodes may be virtual (computed) electrodes from a computerized mapping system, routine or high-resolution ECG mapping electrodes 30, electrodes implanted under or on the skin, or derived from methods to non-invasively detect signals without directly contacting the heart or body. Electrode information may also be derived from stored electrograms in a database 160.

An electrode 25 placed near the heart may be used to modify or destroy regions that are near or at the cause(s) for a rhythm disorder. If the electrode is an ablation catheter, it interfaces to an energy generator 60. Other electrodes may interface with a controller 40, and a pacing module 50, and all desirably communicate with a process controller 70. Ablation or pacing can be directed to nerves supplying the heart 15, which are located at many locations of the heart. Internal ablation electrodes may be replaced with an external ablation system, such as external probes during surgery, or as in external focused irradiation or photon beam as for cancer therapy. In addition, modification of sources, i.e., treatment of the causes of the disorder, may be achieved by delivering appropriate pharmaceutical compositions, gene therapy, cell therapy, or by excluding tissue (at surgery or by using specialized devices).

Process controller 70 may include various components or modules. One such component or module includes a sampling module 80 which is capable of recording signals during the rhythm disorder, recording at various rates not in the rhythm disorder (by pacing), and/or recording during rates that simulate the heart rhythm disorder (by pacing or other methods). Signal amplifiers (not shown) may be used to enhance the signal clarity and strength, and the process controller may also intelligently assign the fewest number of recording amplifiers to sense from a sufficient number of locations to identify and localize the cause. For instance, the system may use fifty to sixty physical amplifier channels to record from 128 sensors (for example, from two commercially available multipolar catheters), by recording those 128 sensors on a 'time-share' basis by time-slicing, or by activating individual/multiple sensors close to a rhythm cause while deactivating others. This 'switching' functionality may be performed by a switching component that connects the sensor device with the electronic control system, and that may be embodied in one or more other components. Switching may be manual or automatic, determined for instance on where causes of the heart rhythm disorder lie. Module 90 interfaces with the pacing module to provide additional heart rates for sensing the biosignal. This is particularly useful for the non-real time mode because it can study the heart at different heart rates even when not in the particular heart rhythm disorder being diagnosed and treated.

The inventive method and system processes the collected data using analytical methods, which may be performed by analytic modules. For example, in FIG. 1A, module 100 is part I of an "Analytic Engine." This portion of the Analytic engine determines the onset and offset for the biologic signal over time, at each sensed location. This is implemented by creating a series of activation times (onset timing) and recovery times (offset timing) during the rhythm over time. The signal is typically represented as voltage over time (that is, as a voltage-time series). Activation time can be processed in many ways. The simplest includes manual assignment at each location. Automated or calculated assignment can be achieved by using zero of the first derivative to define maxima or minima, zero of the second derivative to indicate maximum upstroke or downstroke, or similar methods. Activation onset and offset times can also be assigned when the voltage time-series crosses a threshold. Another possible method to assign activation times is using pattern-matching. For example, a pattern selected to represent the activation duration can be correlated to the signal at multiple time points over time. The time when said correlation values are high indicate recurrences of said template, and thus are considered activation times. The template used for this analysis can also be obtained from stored data in a database, or computed from a rate estimate for the rhythm at that location. Simultaneous recordings from multiple sensors can help in analyzing activation, particularly for complex rhythms such as AF or VF when signal quality may be noisy, of poor quality or show multiple components at different times. From simultaneous recordings, a reference signal is selected, preferably at a nearby location to the channel being analyzed. Signals on the reference channel are used to select signal or signal components on the channel being analyzed. This can be done by using components that retain a similar timing over time, using pattern matching or correlation functions, vectorial analysis or other methods. If many methods are required, heuristics, pattern recognition methods and so-called 'fuzzy logic' approaches can be applied, constrained by known pathophysiology of the atrium.

Module 110 is part II of the Analytic Engine that actually computes and localizes, i.e., determines the existence and location of sources (causes) for the heart rhythm disorder.

Some embodiments of the invention include a "Therapy Engine," which may contain one of more modules designed to cooperatively perform different functions in the system and process. For example, module 120 in FIG. 1A may be responsible for determining the location and migration pattern of sources for the rhythm disorder within the heart. This may be a first module of the Therapy Engine, and is used to compute the location and spatial region which is required to be modified in order to treat or eliminate the rhythm disorder. Treatment may be by delivery of ablation energy or other means as discussed herein, and is not simply one point or region if the source migrates during ablation. Module 130 is representative of another module of the Therapy Engine, and desirably directly interfaces with the energy generator to ablate (destroy), modify (ablate or pace) or stimulate (pace) tissue at sites likely to represent sources. Alternatively, the module 130 may be used to modify tissue without destructive energy, for example by delivering pharmaceutical agents, or gene or cellular therapies.

Module 170 of the system shown in FIG. 1A is representative of a tool to display the identification or location of causes visually or in auditory fashion, to assist the physician in treating or eliminating the rhythm disorder. For example, this module may include a display screen which permits the textual, graphic and/or auditory visualization on the screen of the rotor, focal or other cause of the disorder to be clearly seen by the practitioner. In some embodiments, a "movie" clip of the disorder found will be presented on the screen. This clip is a real-time presentation of the actual cause and location of the disorder. For example, once the analysis of the data has been performed in accordance with the process of the invention, i.e., the location of the signals and their activation onset times have been sequentially ordered, the result of this analysis and computation will be shown on the screen in the form of an activation trail. If the pattern of the activation trail signifies a series of activations revolving around a central core, then a rotor has been found and is in fact a cause of the disorder. Similarly, if the pattern of the activation trail signifies a series of activations which emanate radially from a central core region, then a focal beat has been found and is in fact a cause of the disorder. Thus, this process permits the direct finding of the cause of the disorder and the convenient visualization of the existence, type and location of the disorder for the practitioner. In the event that no discernible pattern is found, i.e., the activation trail is not localized, then additional signal sampling by moving the sensor locations and/or turning-on already placed sensors may be appropriate. The additional signal samples may then be processed and shown on the screen. If a cause is found via the additional sampling and processing of the data, then a decision as to the appropriate treatment may be made. In the event that a dispersed activation trail and pattern is found, further additional sampling may be advisable until such time as the practitioner feels is sufficient. In some instances, the result of the process will render a finding of the existence and location of a rotor or a radially emanating focus. In other instances, where a dispersed pattern remains even after repeated sampling and processing, a diagnosis may be made ruling out a rotor or focal beats as the cause. Thus, the finding of a rotor or a focal point (beat) will be essentially a detection and diagnosis concurrently, whereas the lack of such a finding will be a diagnosis which may rule out the presence of either of these causes of the disorder.

FIG. 2 is a block diagram of a computer system 200. The computer system 200 can include a set of instructions that can be executed to cause the computer system 200 to perform the methods or computer-based functions disclosed herein. The computer system 200 or any portion thereof, may operate as a standalone device or may be connected (e.g., using a network 224) to other computer systems or devices disclosed herein. For example, the computer system 200 can include or be included within any one or more of the catheter, computing device, server, biological sensor, and/or any other devices or systems disclosed herein.

In a networked deployment, the computer system 200 may operate in the capacity of a server or a client machine in a server-client network environment, or a peer machine in a peer-to-peer (or distributed) network environment. The computer system 200 can also be implemented as or incorporated into various devices, such as a personal computer (PC), a tablet PC, a personal digital assistant (PDA), a web appliance, a communications device, a mobile device, a server, client or any other machine capable of executing a set of instructions (sequential or otherwise) that specify actions to be taken by that machine. Further, while a single computer system 200 is illustrated, the term "system" shall also be taken to include any collection of systems or sub-systems that individually or jointly execute a set, or multiple sets, of instructions to perform one or more computer functions.

The computer system 200 can include a processor 202, e.g., a central processing unit (CPU), a graphics-processing unit (GPU), or both. Moreover, the computer system 200 can include a main memory 204 and a static memory 206 that can communicate with each other via a bus 226. As shown, the computer system 200 may further include a video display unit 210, such as a liquid crystal display (LCD), a light emitting diode (LED), a flat panel display, a solid state display, or a cathode ray tube (CRT). Additionally, the computer system 200 may include an input device 212, such as a keyboard, and a cursor control device 214, such as a mouse. The computer system 200 can also include a disk drive unit 216, a signal generation device 222, such as a speaker or remote control, and a network interface device 208.

In some embodiments, the disk drive unit 216 may include a machine or computer-readable medium 218 in which one or more sets of instructions 220 (e.g., software) can be embedded. Further, the instructions 220 may embody one or more of the methods, functions or logic as described herein. The instructions 220 may reside completely, or at least partially, within the main memory 204, the static memory 206, and/or within the processor 202 during execution by the computer system 200. The main memory 204 and the processor 202 may also include computer-readable media.

In an alternative embodiment, dedicated hardware implementations, such as application specific integrated circuits, programmable logic arrays and other hardware devices, can be constructed to implement one or more of the methods, functions or logic described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

According to embodiments of the invention, an analysis method is provided based on phase synchronization of the activation times of a coarse electrode grid. This method has been used demonstrate that AF in humans is consistent with SSWIB and that organization by clinically applied drugs may operate by increasing the spatial domain of a dominant mother rotor. The method employed here is not specific to the details of the electrode array used. The method quantifies the level of synchrony within the tissue covered by the electrode array and is independent of the exact coverage.

The phase synchronization approach employed in embodiments of the inventive method was first evaluated using in silico studies. Activation times in square sheets of two-dimensional (2D) tissue were generated by simulating a standard model for cardiac wave propagation:

$$\partial_t V = D\nabla^2 V - I_{ion}/C_m \quad (1)$$

where V is the transmembrane potential, $C_m$ (µF/cm$^2$) is the membrane capacitance, and $D\nabla^2$ expresses the intercellular coupling via gap junctions. The membrane currents $I_{ion}$ are described by nonlinear evolution equations coupled to V. Details of the model for these currents are not critical to our study, and we present results obtained using the Fenton-Karma model. We coarse grained the computational domain to a similar discrete grid as in the clinical basket electrodes (i.e., an 8×8 grid) and recorded the activation times at the location of the resulting M=64 nodes.

The clinical mapping methodology has been described in detail elsewhere. See, e.g., Narayan S M, et al., "Computational mapping identifies localized mechanisms for ablation of atrial fibrillation," *PLoS One* 7: e46034, 2012, which is incorporated herein by reference. In brief, the method consists of 64 electrode basket catheters that are inserted into both atria, either simultaneously or into the left (LA) or right atrium (RA) sequentially. Unipolar electrograms at each electrode are recorded with a temporal resolution of 1 ms. The basket covers a majority of the atrial tissue and this, combined with a spatial resolution of ~5 mm, allows the determination of reentry waves during AF.

To compute the level of phase synchrony between electrodes, we first converted the activation times from either the in silico data or from the clinical recordings into phase-time information. This was achieved by taking the data of an electrode or, in the case of a simulation, a virtual electrode located within the computational domain, as a periodic event, whereby the activation times mark the beginning of each new cycle. The activation time is then chosen as the time point where the phase has increased by 2π. Between activations, the phase keeps track of how far along a cycle each electrode is in time and is obtained using linear interpolation.

The activation times for the $i^{th}$ electrode are given by $\{t_j^k; k=1, 2, \ldots, N\}$, where N is the total number of activation times. In embodiments of the invention, we utilize activation times marked directly from electrograms recorded during cardiac arrhythmias to compute the time-dependent phase of each region of tissue. The phase of the $i^{th}$ electrogram is defined as $$\varphi_i(t) = 2\pi \frac{t - t_i^k}{t_i^{k+1} - t_i^k} + 2\pi(k-1), \; t_i^k \leq t < t_i^{k+1}, \quad (2)$$

where $t_i^k$ represents the $k^{th}$ activation time of the given electrogram. This phase increases linearly between each sequential activation time, starting at 0, and advances 2π during each electrogram cycle. To determine phase synchrony, we are not concerned with a single electrode's phase, but instead with the time evolution of the phase difference between two electrodes. We can therefore define the time-dependent relative phase between the $i^{th}$ and $j^{th}$ electrode as $\psi_{ij} = n\varphi_i - m\varphi_j$, where n and m are integers. This provides information about the extent to which two separate electrodes' activation dynamics tend to proceed together in time. If the relative phase between electrodes remains constant over a given time period, those electrodes are phase locked and can be said to be synchronized. Note that we are only concerned with how constant the phase difference is with time, and therefore, any global offset in either phase will not affect the results.

If the signal is purely periodic, this synchronization corresponds quantitatively to the phase locking condition $|n\varphi_i - m\varphi_j - \delta| <$ constant, where $\delta$ is an average (constant) phase shift. Because the system is inherently noisy, however, $\psi_{ij}$ fluctuates, resulting in a statistical distribution of the cyclic relative phase $$\psi_{ij} = (\varphi_i - \varphi_j) \bmod 2\pi. \quad (3)$$

To quantify the extent to which these phases are synchronized for a given time period, we then calculate the synchronization number γ as $$\gamma_{ij}^2 = \langle \cos \psi_{ij} \rangle^2 + \langle \sin \psi_{ij} \rangle^2, \quad (4)$$

Here, the quantities inside the brackets are averaged over time. The synchronization number determines the amount of synchrony between the signals from the two electrodes and ranges from γ=0, corresponding to complete asynchrony, and γ=1, corresponding to perfect synchrony (i.e., phase locked), in which case $\psi_{ij}$ has a uniform distribution.

The driving source of the arrhythmia will be determined through the identification of the tissue regions that exhibit distinct patterns of synchrony. These source regions tend to be asynchronous with the global tissue dynamics, owing to atypical activation patterns arising from driver characteristics. In contrast, tissue surrounding the source should be relatively synchronous as it is controlled by this driver.

To determine regions that exhibit different levels of synchrony compared to their surrounding regions, we first compute the distribution of synchronization numbers across all pairs of electrodes, $\gamma_{global}$. Next, for each electrode i, we compute $\gamma_{local}$, the distribution of synchronization numbers between this electrode and all other electrodes. We then define an asynchronous index (ASI), which quantifies the difference between these two distributions and thus the extent to which electrode i records activation dynamics that are atypical from the global trend. Different and standard statistical methods as are known in the art can be used to quantify the difference between the two distributions, $\Delta(\gamma_{local}, \gamma_{global})$, including the Hellinger distance, the Kullback-Leibler divergence, the Bhattacharyya distance, the Kolmogorov-Smirnov test, the Chi-Square test, and others. Rescaling this difference results in a number ranges from 0, if the two distributions are equivalent, to 1, if the two distributions are entirely distinct. We then define ASI as $$ASI_i = \lambda_i \Delta(\gamma_{local}, \gamma_{global}), \quad (5)$$

where $\lambda_i$ is a weighting factor, equal to the mean synchrony of a given electrode's nearest neighbors, included to ensure that the surrounding tissue is itself synchronous, so that elevated ASI is not due to fluctuations around a disorganized state.

As described in D. Vidmar, et al., "Phase synchrony reveals organization in human atrial fibrillation", *Am J Heart Circ Physiol*, 309:H2118-2126, 2015, incorporated herein by reference, the synchronization index (SI) of an electrode is the fraction of synchronized connections between that electrode and all other electrodes:

$$SI_i = \frac{1}{M-1}\sum_{\substack{j=1 \\ j\neq i}}^{M} a_{ij}, \quad (6)$$

Where M is the number of recording electrodes, $\alpha_{ij}$ are entries of either "0" (asynchrony) or "1" (synchrony) in an M×M adjacency matrix. Thus, SI takes on values between 0 and 1 and depends on both the number of synchronized electrodes and the total number of electrodes. If there is a group of m electrodes synchronized with each other, each electrode within this group will have m−1 synchronized connections and an SI value of (m−1)/(M−1). If there is global synchrony over all electrodes, SI=1 for every electrode.

Vidmar, et al. disclose a synchronization index (SI) and provide an example of correlation between SI value and the presence of a focal source. This information describes how a rotor can break down in peripheral tissue using synchrony. What this information doesn't provide is a way of pinpointing the location of the driver/source. It would not enable one to distinguish unorganized domains that are surrounded by organized activity from domains that are unorganized and are not surrounded by organized activity. Furthermore, Vidmar, et al., suggest no comparison of local and global synchrony.

On the other hand, ASI is capable of quantifying how dynamically "out-of-step" a given location (e.g., a point corresponding to an electrode position) is with surrounding tissue. It identifies a local asynchronous area (due to spiral tip meander or other causes) that is surrounded by synchronous tissue. Importantly, if the dynamics of a particular episode are uniform in either organization or disorganization, ASI will be low because Equation 5 measures the dissimilarity of local synchrony as opposed to global synchrony. An elevated value of ASI is therefore only recorded when an electrode's dynamics differ significantly from the global trend, in a manner consistent with a rotor core having a complex tip trajectory. ASI will range from 0 to 1, with higher positive values indicating peculiar dynamical evolution whereas values close to zero indicate evolution in line with the global trend.

We can infer spatial extent of local disorganized regions surrounded by organized regions, and thus the extent of rotor core meander in human AF and VF, through the magnitude of ASI. If disorganization is confined to a single electrode, the value of ASI at that electrode would be large because all neighboring electrodes would be controlled by this source and therefore synchronized with each other. If, instead, disorganization is spread out over multiple electrodes, ASI will be smaller at these sites because some of their neighboring electrodes will themselves be in the domain of disorganization and therefore will be asynchronous. This nearest neighbor asynchrony causes the weighting factor $\lambda_i$ to decrease.

Figure 3:
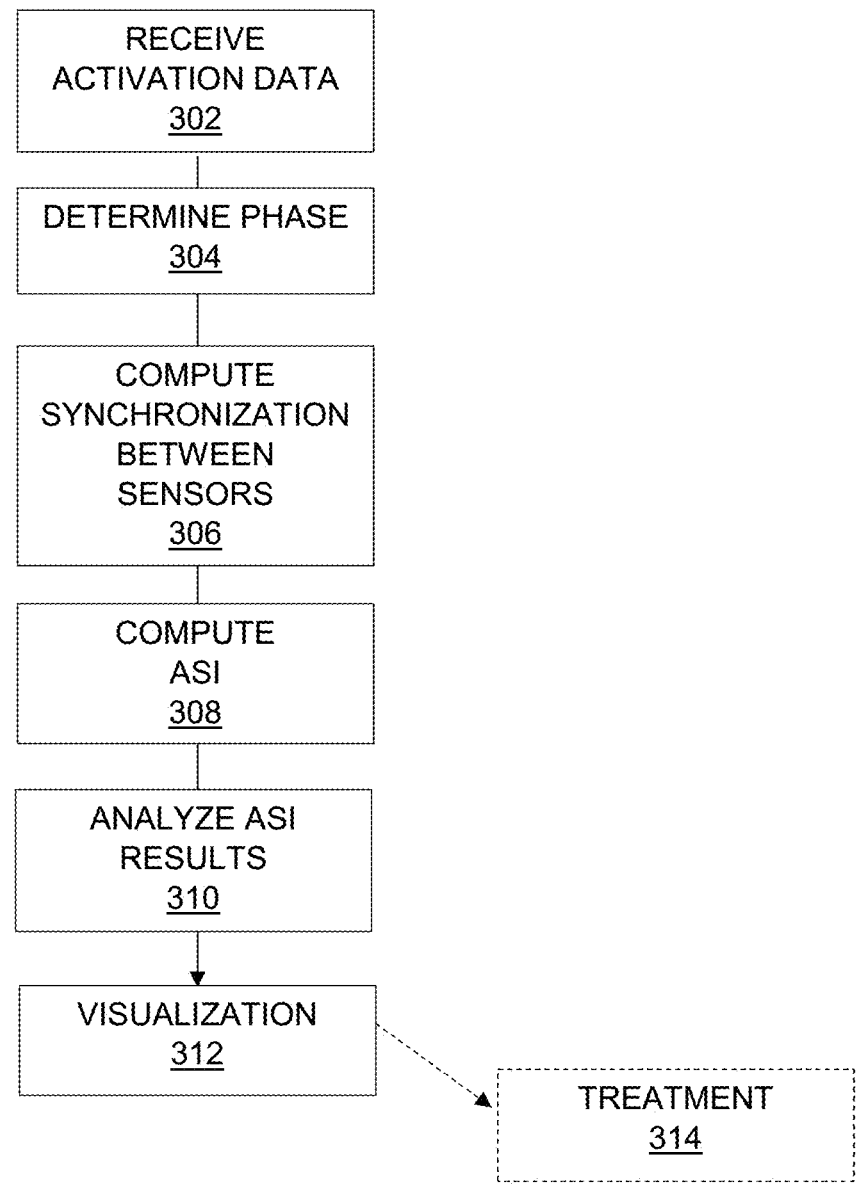
FIG. 3 is a schematic diagram illustrating an embodiment of the inventive method.

FIG. 3 provides a schematic diagram of an embodiment of the inventive method for determining driving sources of heart rhythm disorders, summarizing the procedures described above. In step 302, activation data is provided to a computer processor. The activation data may be obtained directly from a patient via a direct connection to sensors, e.g., electrodes 21, 23, 30, etc., positioned on or in the patient, or may be stored data from prior patient procedures, or may be simulated models, i.e., in silico studies. From the activation data, in step 304, the phase φ is assigned for the signal at every electrode and at every time point using Equation (2). In step 306, synchronization between sensors is computed using Equations (3) and (4). The ASI is computed in step 308 for each sensor according to Equation (5). Analysis of the ASI result for each sensor is performed in step 310 to generate a map or matrix of ASI values across the sensor array. For example, the array illustrated in FIG. 1B would be used to generate a matrix or map of ASI values corresponding to the points on the array. The analysis step would identify areas within the map that have higher ASI values that are at least partially surrounded by synchronous tissue, represented by lower ASI values. Visualization of the resulting ASI map may displayed on a computer monitor, tablet, print-out, or other display device (e.g., video display 210), as a color-coded array, as a grayscale array, or as a matrix of ASI values or alphanumeric characters, where the colors, grayscale, or alphanumeric characters represent ranges of ASI values at the corresponding sensor locations such as those shown in the example of FIG. 1B. This overlapping indicator enables the treating physician to accurately identify the desired location (corresponding to a specific sensor) and apply treatment as appropriate in optional step 314. Treatment may be deferred, or may be administered in conjunction with the testing, in near-real time. For example, where the sensors are catheters configured for delivery of ablation energy, the catheter corresponding to the high ASI value would be activated to modify or destroy the tissue in the high ASI value region.

EXAMPLE 1

Mapping of ASI in Patients with VF

An increasing body of work supports the central role of spiral reentry in maintaining ventricular fibrillation (VF), but current methods rely on manual evaluation of computed phase movies. An embodiment of the automated synchronization analysis was evaluated for its ability identify spiral tip areas during VF corresponding to VF-maintaining sites.

In consecutive patients presenting for ventricular arrhythmia ablation, VF was induced and recorded with 64-electrode basket catheters during defibrillator charging. Electrogram phase was computed from activation times, and synchrony was computed for each pair of electrodes. Areas of elevated Asynchronous Index (ASI), identifying regions of tissue that are dynamically out-of-step with neighboring synchronous tissue, were calculated.

Figure 4A:
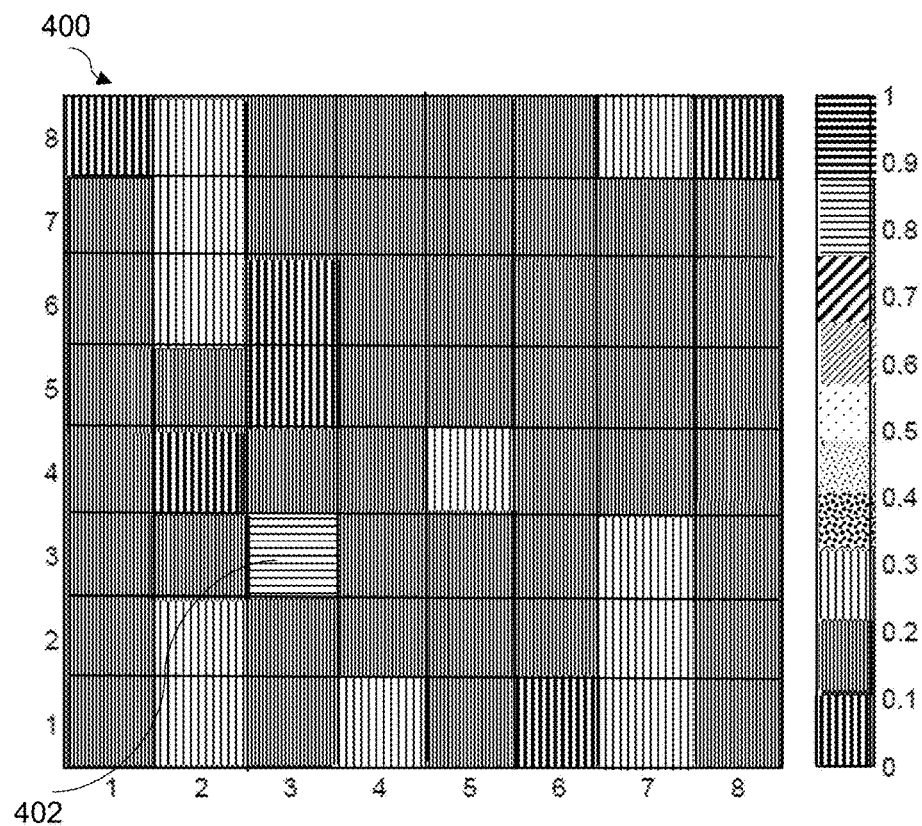
FIG. 4A is an ASI map generated according to the inventive method.
Figure 4B:
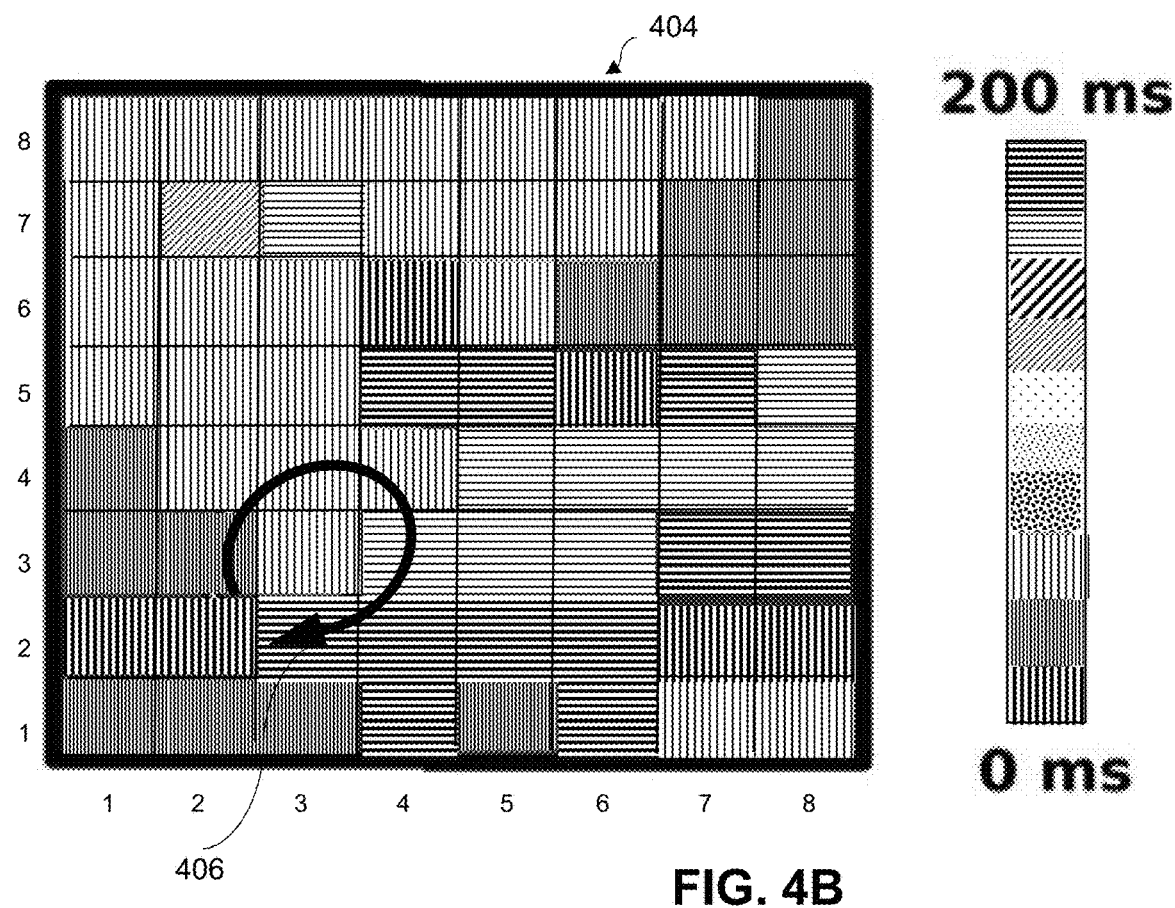
FIG. 4B is an isochronal map showing spiral wave tip area.

Results: of 35 patients enrolled, 23 were successfully induced into VF. Areas of elevated ASI (greater than 0.5) occurred in all sustained episodes of VF. FIG. 4A is an ASI map 400 generated according to an embodiment of the inventive method. In the preferred implementation, color (e.g., RGB) coding would be used to take advantage of the easy discrimination of colors by the normal human eye, with the scale on the right side using an exemplary color scheme of deep red at the top of the scale (1.0) progressing to deep blue or purple at the bottom (0). Alternatively, a grayscale ranging from white to black could also be used. For purposes of illustration, and to comply with the PCT rules, the color red is indicated in both FIGS. 4A and 4B as horizontal to angled lines, for ASI values ~0.7 to 1, while the color blue is indicated by vertical bars, for ASI values 0 to ~0.3. The x- and y-axes of the maps in FIGS. 4A and 4B are 1 through 8 to represent an 8×8 sensor grid. The sensor located at the 3,3 position on the sensor grid, indicated in the figure as position 402, shows an area of elevated ASI=0.85 in a patient. In a color-coded implementation of the display, position 402 would be clearly distinguishable as a red area within a sea of blue. Thus, an elevated value of ASI is displayed where the electrode's dynamics differ from the global trend, which is consistent with a rotor core having a complex tip trajectory. Targeted ablation of the spiral wave tip area, indicated by the black arrow 406 in the isochronal map 404 shown in FIG. 4B, prevented subsequent VF initiation.

Figure 4C:
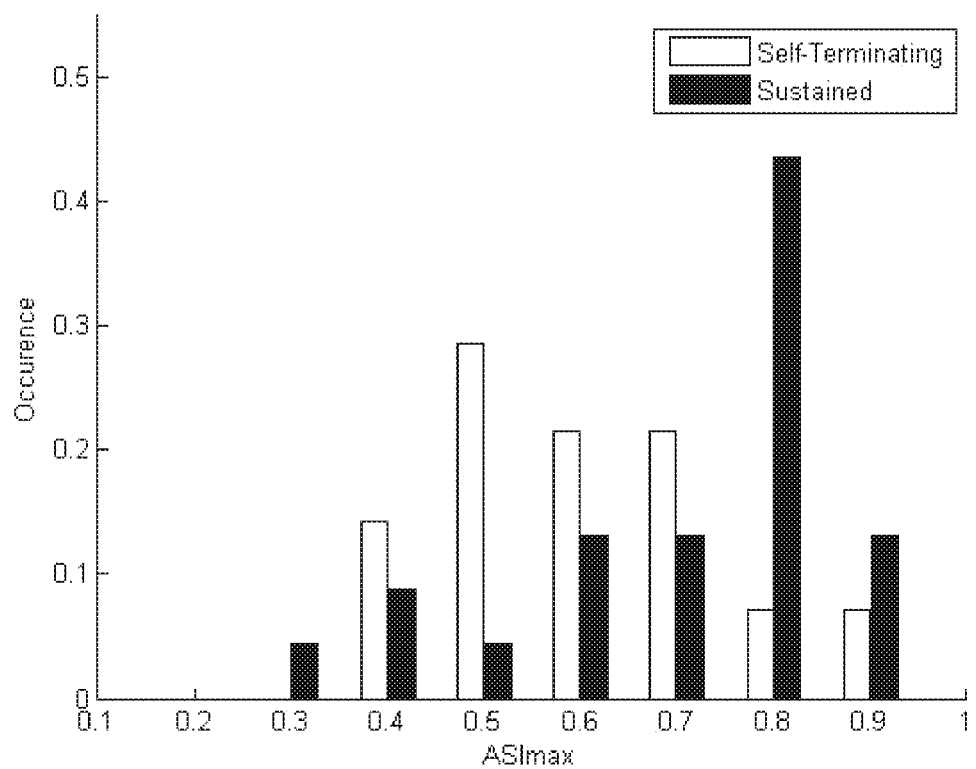
FIG. 4C is a plot comparing ASI with occurrence.

The results of analysis according to an embodiment of the inventive method are provided in FIG. 4C, which is a plot of ASImax versus occurrence during VF, showing the distribution of ASImax. The white bars show the distribution of self-terminating episodes of VF during the first 3 seconds of recording while the black bars show the sustained episodes during the last 3 seconds that data was available in all patients. $ASI_{max}$ was lower in self-terminating episodes (0.60) than in sustained episodes (0.70).

The present invention utilizes quantitative examination of phase synchrony to identify sources that maintain arrhythmias such as VF and AF. As described herein, the driving source of the arrhythmia can be determined through the identification of the tissue regions that exhibit distinct patterns of synchrony. These source regions tend to be asynchronous with the global tissue dynamics due to atypical activation patterns arising from driver characteristics. In contrast, tissue surrounding the source should be relatively synchronous as it is controlled by this driver. By mapping values of synchrony indices in association with sensor locations, an accurate determination of the source can be made for guiding treatment of the arrhythmia.

REFERENCES (INCORPORATED HEREIN BY REFERENCE)

Abreu Filho, C. A. C., L. A. F. Lisboa, et al. (2005). "Effectiveness of the Maze Procedure Using Cooled-Tip Radiofrequency Ablation in Patients with Permanent Atrial Fibrillation and Rheumatic Mitral Valve Disease." Circulation 112(9_suppl): 1-20-25.

Allessie, M. A., J. Ausma, et al. (2002). "Electrical, Contractile and Structural Remodeling during Atrial Fibrillation." Cardiovasc Res 54(2): 230-246.

Bardy, G. H., K. L. Lee, et al. (2005). "Amiodarone or an Implantable Cardioverter-Defibrillator for Congestive Heart Failure." N Engl J Med 352(3): 225-237.

Calkins, H., J. Brugada, et al. (2007). "HRS/EHRA/ECAS expert Consensus Statement on catheter and surgical ablation of atrial fibrillation: recommendations for personnel, policy, procedures and follow-up. A report of the Heart Rhythm Society (HRS) Task Force on catheter and surgical ablation of atrial fibrillation. European Heart Rhythm Association (EHRA); European Cardiac Arrhythmia Society (ECAS); American College of Cardiology (ACC); American Heart Association (AHA); Society of Thoracic Surgeons (STS)." Heart Rhythm 4(6): 816-61.

Cappato, R., H. Calkins, et al. (2005). "Worldwide Survey on the Methods, Efficacy, and Safety of Catheter Ablation for Human Atrial Fibrillation." Circulation 111(9): 1100-1105.

Cappato, R., H. Calkins, et al. (2009). "Prevalence and causes of fatal outcome in catheter ablation of atrial fibrillation." J Am Coll Cardiol 53(19): 1798-803.

Cheema, A., C. R. Vasamreddy, et al. (2006). "Long-term single procedure efficacy of catheter ablation of atrial fibrillation" J Intery Card Electrophysiol 15(3): 145-155.

Cox, J. L. (2004). "Cardiac Surgery for Arrhythmias." J Cardiovasc Electrophysiol. 15: 250-262.

Cox, J. L. (2005). "The central controversy surrounding the interventional-surgical treatment of atrial fibrillation." J. Thorac. Cardiovasc. Surg. 129(1): 1-4.

Ellis, E. R., S. D. Culler, et al. (2009). "Trends in utilization and complications of catheter ablation for atrial fibrillation in Medicare beneficiaries." Heart Rhythm 6(9): 1267-73.

Gaspo, R., R. F. Bosch, et al. (1997). "Functional Mechanisms Underlying Tachycardia-Induced Sustained Atrial Fibrillation in a Chronic Dog Model." Circulation 96(11): 4027-4035.

Kalifa, J., K. Tanaka, et al. (2006). "Mechanisms of Wave Fractionation at Boundaries of High-Frequency Excitation in the Posterior Left Atrium of the Isolated Sheep Heart During Atrial Fibrillation." Circulation 113(5): 626-633.

Knecht, S., F. Sacher, et al. (2009). "Long Term Follow-Up of Idiopathic Ventricular Fibrillation Ablation: A Multicenter Study." J Am Coll Cardiol 54(6): 552-528.

Masse, S., E. Downar, et al. (2007). "Ventricular fibrillation in myopathic human hearts: mechanistic insights from in vivo global endocardial and epicardial mapping." Am J Physiol Heart Circ Physiol 292(6): H2589-97.

Moe et al., "A Computer Model of Atrial Fibrillation," Am Heart J, 20, 67 (1964).

Myerburg, R. J. and A. Castellanos (2006). "Emerging paradigms of the epidemiology and demographics of sudden cardiac arrest." Heart Rhythm 3(2): 235-239.

Nademanee, K., J. McKenzie, et al. (2004a). "A new approach for catheter ablation of atrial fibrillation: mapping of the electrophysiologic substrate." J Am. Coll. Cardiol. 43(11): 2044-2053.

Narayan, S. M., D. E. Krummen, et al. (2006d). "Evaluating Fluctuations in Human Atrial Fibrillatory Cycle Length Using Monophasic Action Potentials." Pacing Clin Electrophysiol 29(11): 1209-1218.

Nash, M. P., A. Mourad, et al. (2006). "Evidence for Multiple Mechanisms in Human Ventricular Fibrillation" Circulation 114: 536-542.

Ng, J., A. H. Kadish, et al. (2006). "Effect of electrogram characteristics on the relationship of dominant frequency to atrial activation rate in atrial fibrillation." Heart Rhythm 3(11): 1295-1305.

Ng, J., A. H. Kadish, et al. (2007). "Technical considerations for dominant frequency analysis." J Cardiovasc Electrophysiol 18(7): 757-64.

Oral, H., A. Chugh, et al. (2007). "Radiofrequency catheter ablation of chronic atrial fibrillation guided by complex electrograms." Circulation 115(20): 2606-12.

Oral, H., A. Chugh, et al. (2009). "A randomized assessment of the incremental role of ablation of complex fractionated atrial electrograms after antral pulmonary vein isolation for long-lasting persistent atrial fibrillation." J Am Coll Cardiol 53(9): 782-9.

Reddy, V. Y., M. R. Reynolds, et al. (2007). "Prophylactic catheter ablation for the prevention of defibrillator therapy." N Engl J Med 357(26): 2657-65.

Ryu, K., S. C. Shroff, et al. (2005). "Mapping of Atrial Activation During Sustained Atrial Fibrillation in Dogs with Rapid Ventricular Pacing Induced Heart Failure: Evidence for a Role of Driver Regions." *Journal of Cardiovascular Electrophysiology* 16(12): 1348-1358.

Sahadevan, J., K. Ryu, et al. (2004). "Epicardial Mapping of Chronic Atrial Fibrillation in Patients: Preliminary Observations." *Circulation* 110(21): 3293-3299.

Sanders, P., O. Berenfeld, et al. (2005a). "Spectral Analysis Identifies Sites of High-Frequency Activity Maintaining Atrial Fibrillation in Humans." *Circulation* 112(6): 789-797.

Singh, B. N., S. N. Singh, et al. (2005). "Amiodarone versus Sotalol for Atrial Fibrillation." *N Engl J Med* 352 (18): 1861-1872.

Skanes, A. C., R. Mandapati, et al. (1998). "Spatiotemporal Periodicity During Atrial Fibrillation in the Isolated Sheep Heart." *Circulation* 98(12): 1236-1248.

Tabereaux, P. B., G. P. Walcott, et al. (2007). "Activation patterns of Purkinje fibers during long-duration ventricular fibrillation in an isolated canine heart model." *Circulation* 116(10): 1113-9.

Vaquero, M., D. Calvo, et al. (2008). "Cardiac fibrillation: From ion channels to rotors in the human heart." *Heart Rhythm,* 5(6): 872-879.

D. Vidmar, et al., "Phase synchrony reveals organization in human atrial fibrillation", *Am J Heart Circ Physiol,* 309:H2118-2126, 2015.

Waldo, A. L. and G. K. Feld (2008). "Inter-relationships of atrial fibrillation and atrial flutter mechanisms and clinical implications." *J Am Coll Cardiol* 51(8): 779-86.

Warren, M., P. K. Guha, et al. (2003). "Blockade of the inward rectifying potassium current terminates ventricular fibrillation in the guinea pig heart." *J Cardiovasc Electrophysiol* 14(6): 621-31.

Wijffels, M. C., C. J. Kirchhof, et al. (1995). "Atrial fibrillation begets atrial fibrillation: a study in awake chronically instrumented goats." *Circulation* 92: 1954-1968.

The invention claimed is:

1. A method for determining a source of a cardiac rhythm disorder in a patient suspected of having the cardiac rhythm disorder, comprising:
    collecting, via a computer processor, a plurality of cardiac signals at a plurality of locations during a cardiac arrhythmia;
    identifying activation times within the cardiac signals;
    computing time-dependent phase of each region of tissue;
    computing a level of phase synchrony between a plurality of pairs of locations within the plurality of locations to assign a synchronization number within a range of numbers corresponding to complete asynchrony and complete synchrony for each pair of locations; and
    generating a spatial synchrony map using the synchronization numbers to identify one or more asynchronous tissue regions surrounded by regions of synchrony in the patient's heart.

2. The method of claim 1, wherein the synchronization number is computed according to the relationship $\gamma_{ij}^2 = \langle \cos \psi_{ij} \rangle^2 + \langle \sin \psi_{ij} \rangle^2$, where $\psi_{ij}$ is the cyclic relative phase, $\psi_{ij} = (\varphi_i - \varphi_j) \mod 2\pi$.

3. The method of claim 1, wherein the step of generating comprises computing and comparing local and global distributions of synchronization number.

4. The method of claim 3, wherein comparison of local and global distributions of synchronization number further comprises quantifying a difference in the distributions.

5. The method of claim 4, wherein quantifying differences in the distributions comprises using a method selected from the group consisting of Hellinger distance, the Kullback—Leibler divergence, the Bhattacharyya distance, the Kolmogorov-Smirnov test, and the Chi-Square test.

6. The method of claim 4, further comprising assigning an Asynchronous Index (ASI) to the difference and associating the ASI with a specific location of the plurality of locations.

7. The method of claim 6, further comprising displaying a map of ASI comprising visually-encoded regions corresponding to the locations.

8. The method of claim 7, wherein the visually-encoded regions are indicated by a visually-distinguishable scale selected from color, grayscale, and alphanumeric character labels.

9. The method of claim 1, further comprising, prior to collecting, inducing the cardiac arrhythmia.

10. The method of claim 1, wherein the range of numbers corresponding to complete asynchrony and complete synchrony is from "0" to "1".

11. A system for determining a source of a cardiac rhythm disorder in a patient suspected of having the cardiac rhythm disorder, the system comprising:
    a computer processor programmed to execute the steps of:
        collecting a plurality of cardiac signals at a plurality of locations during a cardiac arrhythmia;
        identifying activation times within the cardiac signals;
        computing time-dependent phase of each region of tissue;
        computing a level of phase synchrony between a plurality of pairs of locations within the plurality of locations to assign a synchronization number within a range of numbers corresponding to complete asynchrony and complete synchrony for each pair of locations; and
        generating a spatial synchrony map using the synchronization numbers to identify one or more asynchronous tissue regions surrounded by regions of synchrony in the patient's heart.

12. The system of claim 11, wherein the synchronization number is computed according to the relationship $\gamma_{ij}^2 = \langle \cos \psi_{ij} \rangle^2 + \langle \sin \psi_{ij} \rangle^2$, is the cyclic relative phase, $\psi_{ij} = (\varphi_i - \varphi_j) \mod 2\pi$.

13. The system of claim 11, wherein the computer processor is further programmed to execute the step of computing and comparing local and global distributions of synchronization number.

14. The system of claim 13, wherein the computer processor compares local and global distributions of synchronization number by quantifying a difference in the distributions.

15. The system of claim 14, wherein the computer processor quantifies differences in the distributions using a method selected from the group consisting of Hellinger distance, the Kullback—Leibler divergence, the Bhattacharyya distance, the Kolmogorov-Smirnov test, and the Chi-Square test.

16. The system of claim 14, wherein the computer processor further assigns an Asynchronous Index (ASI) to the difference and associates the ASI with a specific location of the plurality of locations.

17. The system of claim 16, further comprising a visual display device, wherein the computer processor causes the visual display device to display a map of ASI comprising visually-encoded regions corresponding to the locations.

18. The system of claim 17, wherein the visually-encoded regions are indicated by a visually-distinguishable scale selected from color, grayscale, and alphanumeric character labels.

19. The system of claim 11, further comprising a device for inducing the cardiac arrhythmia.

20. The system of claim 11, further comprising a sensor array defining a grid corresponding to locations within the patient's heart.

21. The system of claim 11, wherein the range of numbers corresponding to complete asynchrony and complete synchrony is from "0" to "1".

* * * * *